(12) United States Patent
Tu et al.

(10) Patent No.: US 7,004,911 B1
(45) Date of Patent: Feb. 28, 2006

(54) OPTICAL THERMAL MAPPING FOR DETECTING VULNERABLE PLAQUE

(76) Inventors: Hosheng Tu, 15 Riez, Newport Beach, CA (US) 92657; Winston Z. Ho, 14541 Langhill Dr., Hacienda Heights, CA (US) 91745

( * ) Notice: Subject to any disclaimer, the term of this patent is extended or adjusted under 35 U.S.C. 154(b) by 376 days.

(21) Appl. No.: 10/373,539

(22) Filed: Feb. 24, 2003

(51) Int. Cl.
*A61B 5/00* (2006.01)

(52) U.S. Cl. ...................................................... 600/549

(58) Field of Classification Search ............ 606/15–17, 606/13, 10, 2, 41, 21, 28; 607/88, 92; 604/20; 501/4, 7, 10; 356/300; 600/504, 310, 342, 600/473, 549, 474
See application file for complete search history.

(56) References Cited

U.S. PATENT DOCUMENTS

| | | | |
|---|---|---|---|
| 5,444,803 A | 8/1995 | Kim et al. | |
| 5,627,927 A | 5/1997 | Udd | |
| 5,646,401 A | 7/1997 | Udd | |
| 5,871,449 A * | 2/1999 | Brown | 600/474 |
| 5,924,997 A | 7/1999 | Campbell | |
| 6,018,160 A | 1/2000 | Bennion et al. | |
| 6,072,922 A | 6/2000 | Albin et al. | |
| 6,087,280 A * | 7/2000 | Beall et al. | 501/7 |
| 6,143,018 A * | 11/2000 | Beuthan et al. | 607/88 |
| 6,245,026 B1 | 6/2001 | Campbell et al. | |
| 6,292,695 B1 | 9/2001 | Webster, Jr. et al. | |
| 6,319,251 B1 | 11/2001 | Tu et al. | |
| 6,335,524 B1 | 1/2002 | Udd et al. | |
| 6,422,084 B1 | 7/2002 | Fernald et al. | |
| 6,450,971 B1 | 9/2002 | Andrus et al. | |
| 6,459,486 B1 | 10/2002 | Udd et al. | |
| 6,475,159 B1 | 11/2002 | Casscells et al. | |
| 6,475,210 B1 | 11/2002 | Phelps et al. | |
| 6,514,214 B1 | 2/2003 | Kokate et al. | |
| 6,635,052 B1 * | 10/2003 | Loeb | 606/15 |
| 6,716,178 B1 * | 4/2004 | Kilpatrick et al. | 600/504 |
| 2003/0060820 A1 * | 3/2003 | Maguire et al. | 606/41 |
| 2004/0111016 A1 * | 6/2004 | Casscells et al. | 600/310 |

OTHER PUBLICATIONS

Zarrabi A., et al., "Intravascular Thermography : A Novel Approach For Detection of Vulnerable Plaque" Current Opinion in Cardiology 2002; 17: 656-662.
Liu Sy et al., "Highly Sensitive Long Period Fibre Grating Temperature Sensor" Photonics Systems and Applications (Sidorin YS & Tang D. Editors), Proceedings of SPIE vol. 459 (2001) pp. 282-286.
Qiao X et al., "Distributed Optic Fiber Bragg Grating Sensor For Simulaneous Measurments Of Pressure And Temperature In The Oil And Gas Downhole", Active and Passive Optical Components For WDM Communications II (Dutta AK, Awwal AAS, Dutta NK & Okamoto K, Editors) Proceedings of SPIE vol. 4870 (2002) pp. 554-558.

(Continued)

*Primary Examiner*—Max F. Hidenburg
*Assistant Examiner*—Brian Szmal

(57) ABSTRACT

An optical thermal device and methods for monitoring temperature and detection of a vulnerable plaque of a patient comprising an elongate tubular element comprising at least one optical fiber; the fiber having at least one optical grating along an axis of the fiber; and a light source having a light beam that is coupled into the at least one optical fiber; wherein the optical grating reflects a certain wavelength or intensity of the light beam, the certain wavelength or intensity of the reflected light beam being correlated to the temperature of the tissue regions.

19 Claims, 9 Drawing Sheets

OTHER PUBLICATIONS

Nishi H et al., "Temperature Sensor Using A Long-Period Fiber Grating" Optical Engineering For Sensing And Nanotechnology (Iwata K, Editor) Proceedings Of SPIE vol. 4416 (2001) pp. 166-169.

Protopov VN et al., "Temperature Sensor Based On Fiber Bragg Grating" Advances In Fiber Optics (Dianov EM, Editor) Proceedings of SPIE vol. 4083 (2000), pp. 224-227.

* cited by examiner

OPTICAL THERMAL MAPPING FOR DETECTING VULNERABLE PLAQUE

FIELD OF THE INVENTION

The present invention is generally related to an optical thermal mapping device for measuring the intravascular vessel temperature in vivo with high spatial and temperature resolution. More particularly, the present invention relates to an optical thermal mapping device comprising multiple optical fibers and multiple optical gratings for simultaneously monitoring the thermal distribution of and detecting vulnerable plaque within a blood vessel.

BACKROUND OF THE INVENTION

Vulnerable plaques are atherosclerotic plaques associated with erosion and ulceration that prone to rupture leading to acute embolization and thrombus. Until recently, physicians believed that most heart attacks were caused by a gradual buildup of atherosclerotic plaque in the arteries of the heart that eventually impeded blood flow. In fact, up to half of all sudden, out-of-hospital cardiac deaths occur in people with no prior diagnosis of heart disease and over two-thirds of heart attack suffers have blockages in their arteries considered to be clinically insignificant in terms of plaque burden and percent stenosis.

Most ruptured plaques are characterized by a large lipid pool and a thin fibrous cap with macrophage infiltration. On the other hand, calcified plaque deposits typically comprise hard material that restricts blood flow in a blood vessel. But, atherosclerotic plaque may also comprise combinations of soft and hard materials. The main difference between a soft vulnerable plaque and a hard stable plaque lies in the risk for a vulnerable plaque to rupture suddenly. The risk of plaque rupture is greatest when the fibrous cap is very thin or the plaque lipid pool is very large.

The buildup of plaque in the blood vessels is sometimes referred to as atherosclerosis, or hardening of the arteries. Atherosclerosis often begins as a small injury to an artery wall. This injury triggers a cascade of injury and response, inflammation, and healing, which may ultimately lead to the narrowing of the artery. It is generally believed that inflammation in an arterial plaque is the result of a series of biochemical and mechanical changes in the arterial wall. The inflammatory cells collect the debris of the damaged tissue resulting in a core of lipid, including macrophages or foam cells and necrotic tissue that is covered by a thin fibrous cap of scar tissue. If the fibrous cap becomes weakened, eroded, or is subjected to excessive mechanical stress, it may rupture and expose the thrombogenic damaged endothelium and metabolic byproducts to the blood stream that causes blood clotting. If the resulting blood clot is severe enough, it may occlude the artery. If this obstruction persists in a coronary artery, a myocardial infarction or angina may result.

Many vulnerable plaque deposits do not obstruct the flow of blood through the blood vessels. Vulnerable plaques are often undetectable using conventional techniques such as angiography. However, a plaque may rupture suddenly and form a blood clot in the blood vessel lumen causing a blockage and causes heart attack and death. Recently, inflammation has been recognized being associated with the formation and progression of vulnerable plaques. An increase in tissue temperature at a lesion is thought to be caused by the response of the immune system to inflammation and an increase in metabolic activity involved in the healing process. It has been observed that the inflamed necrotic core of a vulnerable plaque maintains itself at a temperature which may be a fraction of a degree to a few degrees higher than the surrounding tissue. Vulnerable plaques are generally characterized by hemodynamically insignificant, variable in size, not calcified, and undetectable with standard anatomic imaging methods.

The inability of common diagnostic methodologies, such as coronary angiography that is the current gold standard technique for diagnosing coronary vessel obstructions, to detect vulnerable plaque has led to a major rush to develop new methods to detect, characterize and treat patients with these types of deposits. Unlike the typical occlusive atherosclerotic lesion, vulnerable plaque deposits are associated with a compensatory enlargement of the vessel wall known as positive lumen remodeling. Selected intravascular imaging techniques for vulnerable plaque include angioscopy, intravascular ultrasound, thermography, optical coherence tomography, elastography, magnetic resonance imaging, nuclear imaging, electrical impedance imaging, shear stress imaging, photonic spectroscopy, and the like. Among them, catheter-based intravascular thermography is the most promising one, which is based on the premise that vulnerable plaques are hotter than surrounding normal tissue and that by measuring these temperature elevation, physicians can determine the exact location and extent of disease.

Casscells and associates (Current Opinion in Cardiology 2002; 17:656–662) reported mechanism of heat production in atherosclerotic plaques by a high metabolic rate in the areas of macrophage accumulation, of which a sub-population strongly expresses mitochondrial uncoupling proteins. The uncoupling proteins are homologs of thermogenin, which is responsible for thermogenesis in brown fat tissue. Further, they measured temperature of living samples with a thermistor and found that plaques showed several regions in which the surface temperatures varied reproducibly by 0.2° C. to 0.3° C. Infrared thermographic images also revealed heterogeneity in temperature among the plaques.

U.S. Pat. No. 5,924,997 to Campbell, entire contents of which are incorporated herein by reference, discloses an intravascular catheter system capable of mapping thermal variations in the temperature of atherosclerotic plaque by a plurality of thermal sensors fixedly attached along the catheter. The thermal sensors are mounted on the catheter shaft and soldered to a conductor while each sensor needs a conductor. The spacing of the mechanical thermal sensors arrangement allows only limited sensors to be placed within a unit length.

U.S. Pat. No. 6,292,695 to Webster, Jr. et al., entire contents of which are incorporated herein by reference, discloses a basket shaped catheter with a plurality of electrodes on each expandable member of the basket, while each electrode may comprise a thermal sensor for temperature monitoring. The spacing of the electrodes with mechanical thermal sensors arrangement allows only limited sensors to be placed within a unit length on each expandable member of the basket.

U.S. Pat. No. 6,450,971 to Andrus et al., entire contents of which are incorporated herein by reference, discloses a balloon catheter having temperature responsive material designed to exhibit at least one predetermined color when the material is in contact with an object having an elevated temperature, wherein a light detector positioned to indirectly detect the color change indicative of suspected lesion. The Andrus et al. balloon catheter uses a moving light detector to map multiple lesion sites within a blood vessel.

U.S. Pat. No. 6,475,159 to Casscells et al, entire contents of which are incorporated herein by reference, discloses an infrared heat-sensing catheter using an infrared fiberoptic system at the tip of the catheter to locate a single inflamed, heat-producing atherosclerotic plaque. The Casscells et al. catheter uses a dragging method to map multiple lesion sites within a blood vessel.

U.S. Pat. No. 6,514,214 to Kokate et al., entire contents of which are incorporated herein by reference, discloses a catheter with at least one temperature sensor disposed proximate to the distal end of the elongate shaft adapted to contact an inner surface of the blood vessel. The Kokate et al. catheter uses a dragging method to map multiple lesion sites within a blood vessel.

None of the above-identified patents discloses a thermal sensing means for measuring a plurality of contiguous points without dragging the device for area thermal mapping. Therefore, to overcome the disadvantages of the above-cited thermal sensing catheters, it is one aspect of the present invention to provide an optical thermal mapping device and methods for simultaneously monitoring the thermal distribution of and detecting vulnerable plaques within a blood vessel on a real time basis.

The thermal mapping of vulnerable plaques using at least one optical fiber and multiple optical gratings are disclosed herein. Optical fibers are hair thin strands of glass that guide light. The optical fiber has an inner core surrounded by an outer cladding. In order to guide light, the core refractive index is higher than the cladding index. A fiber grating, which the periodic structure of the refractive index is formed inside the core of a fiber, is widely used in the field of fiber-optic communication for wavelength management. The optical grating reflects or transmits a certain portion, wavelength (bandwidth) or intensity, of the light along optical fibers. A fiber Bragg grating is based on the interference of multiple reflection of a light beam in a fiber segment whose index of refraction varies periodically along the length of the fiber. Variations of the refractive index constitute discontinuities that emulate a Bragg structure. If the spacing of the index periods is equal to one half of the wavelength of the light, then the waves will interfere constructively (the round trip of each reflected wave is one wavelength) and a large reflection will occur from the periodic array. Optical signals whose wavelengths are not equal to one half the spacing will travel through the periodic array unaffected.

A periodic variation of the refractive index is formed by exposing the core, such as germanosilicate, of the fiber to an intense ultraviolet (UV) optical interference pattern or mask that has a periodicity equal to the periodicity of the grating to be formed. When the fiber is exposed to an intensive UV pattern, structural defects are formed and thus a permanent variation of the refractive indexes having the same periodicity with the UV pattern. The condition for strong reflection of Bragg wavelength is $\lambda = 2 \times n \times d$. Where n is the effective refractive index, and d is Bragg spacing or grating period. Both n and d change with changes in temperature due to thermal-optic and thermal expansion effects.

The merits of optical fiber sensors include immunity to electromagnetic interference, high flexibility, remote sensing capability, smaller size of sensing element, lightweight, and easy to fabricate. Optical fiber sensors have been developed for chemical, strain, temperature and pressure sensing, and smart structure inspection. Various fiber-grating configurations have been developed for sensor application. Depending on its configuration, in general, it can be classified as direct and indirect sensors. Direct sensors measure the environmental effects surrounding the grating. Indirect sensors measure the environmental effects at the tip of the fiber and use fiber grating for wavelength management. The sensing signal is obtained through either a transmission or reflection mode. In some aspect of the present invention, it is provided direct fiber grating as direct sensors in a reflection mode.

Fiber gratings reflect light of particular bandwidth, and can act as high-performance optical thermal sensor. The reflected bandwidths are extremely narrow because of the long path lengths possible in optical fibers. Therefore, a minute temperature change surrounding the fibers changes the effective refractive index and grating's periods, thus modulating their reflective wavelength or intensity. When multiple gratings are created in an optic fiber, a multi-point sensor can be monitored simultaneously.

Fiber-grating technologies have been proven and demonstrated with excellent sensing abilities for temperature, pressure, stress and various chemicals detection. They also exhibit extremely long-term stability, and minimal optical losses. Several prior art devices have been described for the performance of a number of optical fiber grating sensors. U.S. Pat. No. 5,627,927 discloses an interferometer fiber grating for sensing the environmental effect at the termination of the fiber. U.S. Pat. No. 6,072,922 discloses a cryogenic fiber optical sensor by introducing additional thermal strain in the fiber to enhance sensor sensitivity. U.S. Pat. No. 5,444,803 discloses a fiber-optic device includes fiber grating and mode stripper to admit only one mode for sensor application. U.S. Pat. No. 6,018,160 discloses an apparatus using two optical gratings for sensing aircraft skin temperature and/or strain. The above-referred patents, U.S. Pat. Nos. 5,627,927, 6,072,922 5,444,803, and 6,018,160, entire contents of all being incorporated herein by reference, disclose fiber-grating technology suitably applicable in the present invention.

Although many prior art patents are related to optical grating sensor, none of them discloses a medical device system and methods combining multiple grating in multiple fibers formed in a basket configuration for intravascular temperature measurement in vivo. In one aspect, the optical thermal device system with thermographic mapping capability offers high spatial and temperature resolution for simultaneously monitoring the thermal distribution of and detecting vulnerable plaque within a blood vessel.

SUMMARY OF THE INVENTION

In accordance with preferred embodiments of the present invention, an optical thermal basket catheter is provided for intravascular measurement of the temperature of a vessel wall. In one aspect of the present invention, it is provided an optical thermal basket catheter comprising an elongate catheter sheath having a lumen, a distal sheath end, and a proximal sheath end; a plurality of optical fibers deployably disposed within the lumen of the catheter sheath, each fiber having a distal fiber portion, a distal fiber end and a proximal fiber end, wherein the plurality of distal fiber portions is suitably expandable in an outwardly radial manner adapted for forming a basket shape and for contacting at least a portion of the vessel wall. Each fiber has at least one optical grating along an axis of the fiber; and a light source has a light beam, wherein the light beam is coupled into the plurality of optical fibers, wherein the at least one optical grating reflects a certain wavelength or intensity of the light beam, the certain wavelength or intensity of the reflected light beam being correlated to the temperature of the portion of the vessel wall.

Another object of this invention is to provide a ready to use, highly sensitive and accurate catheter-based optical fiber sensor system for detecting vulnerable plaque. Thermographic images reveals heterogeneity in temperature profiles among the vulnerable plaques.

Another object of this invention is to provide a ready to use, highly sensitive and accurate device-based optical fiber sensor probe for detecting inflammation in coronary arteries or tissue regions such as a breast or a heart, wherein the probe is a catheter, a cannula or a hollow needle with side opening. In some aspect, it is provided an optical thermal device for monitoring temperature of a tissue region of a patient comprising an elongate tubular element comprising at least one optical fiber that contacts the tissue region; the at least one optical fiber having at least one optical grating along an axis of the fiber; and a light source having a light beam, wherein the light beam is coupled into the at least one optical fiber. The at least one optical grating along the axis of the fiber reflects a certain wavelength or intensity of the light beam, the certain wavelength or intensity of the reflected light beam being correlated to the temperature of the tissue region.

Another object of this invention is to combine a 4-French or smaller catheter with an expandable and externally controllable basket with multiple build-in flexible optical fibers, each fiber with multiple gratings, for suitably accessing an intravascular vessel and measuring the local temperature distribution of the vessel wall.

Another object of this invention is to provide an optical thermal device or an optical thermal basket catheter by using optical fiber gratings with thermal resolution of 0.01° C. to 5.0° C., preferably between 0.01° C. and 1.0° C.

It is a further object of the present invention to provide an optical thermal device or an optical thermal basket catheter by using optical fiber gratings having a length between 0.2 and 40 mm.

In still another aspect of the present invention, it is provided a method for monitoring temperature of a tissue region of a patient, the method comprising deploying an elongate tubular element into contacting the tissue region, wherein the elongate tubular element comprises at least one optical fiber. The fiber has at least one optical grating along an axis of the fiber, and a light source having a light beam is coupled into the at least one optical fiber; the optical grating reflecting a certain wavelength or intensity of the light beam, and the certain wavelength or intensity of the reflected light beam being correlated to the temperature of the tissue region.

The present optical fiber medical device has the advantages of simple, real-time, and easy operation. The probe also provides accurate and reproducible results. It should be understood, however, that the detail description and specific examples, while indicating preferred embodiments of the present invention, are given by way of illustration and not of limitation. Further, as will become apparent to those skilled in the art, the teaching of the present invention can be applied to medical devices for measuring temperature at a variety of body parts.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY MBODIMENTS

The preferred embodiments of the present invention described below relate particularly to an optical thermal mapping device comprising at least one optical fiber and multiple optical gratings for simultaneously monitoring the thermal distribution of and detecting vulnerable plaque within a blood vessel. While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described below.

Figure 1:
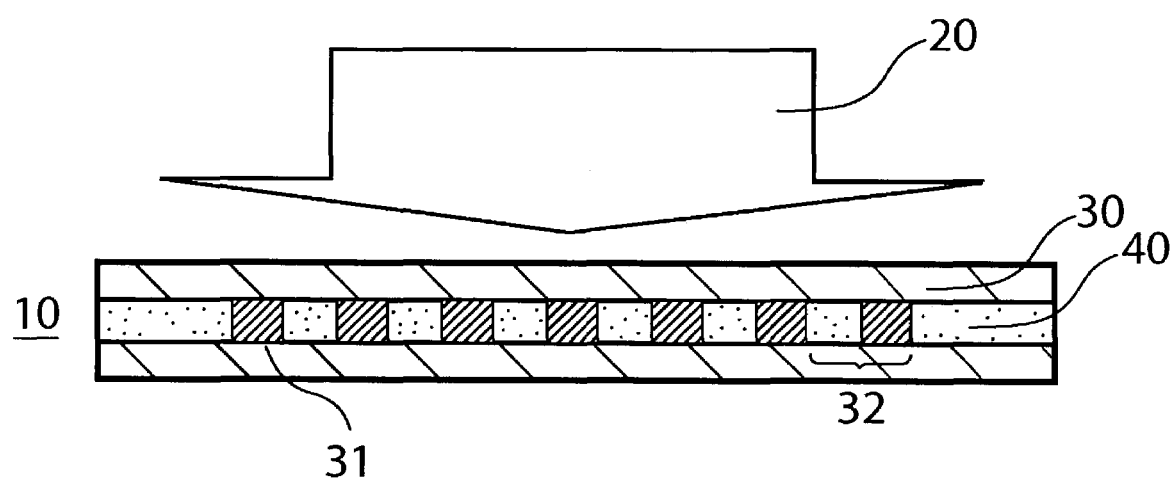
FIG. 1 is a fiber with a Bragg grating made by a UV interference pattern.

The optic fiber grating principles are briefly described herein for reference. The creation of high performance optical components by photolithographically writing periodic variations in the refractive index—"Bragg grating"—directly into the cores of conventional silica-based fibers. Regardless of the method used, the interference pattern must be of high quality, with uniform periodicity, high contrast, and sharp edges. The UV periodicity, as shown in FIG. 1, is formed by means of one of several optical methods (for example, UV mask, diffraction, interferometry, or the like) that generate an interference pattern of alternating minima and maxima of light intensity. The UV source 20 is provided by an excimer laser that operates at a wavelength in the 157–351 nm. The UV or near UV light pattern transmits through the cladding 30 and creates an index perturbation (Δn) 31 with a periodicity 32 in the core 40 of the fiber 10 that depends on the wavelength band in which the grating is designed to operate.

The grating reflectivity, R, for a given mode at enter wavelength (λ) is given by $$R = \tanh^2[L\Delta n \eta(V)/\lambda]$$

Where L is the length of the grating, Δn is the magnitude of index perturbation, and η (V) a function of fiber parameter V that represents the fraction of the integrated mode intensity contained in the core 40. The core diameter of the single mode fiber is typically less than 10 μm, while the total fiber diameter is approximately 0.1–2 mm. A smaller optic fiber of less than 100 μm may also be useful in certain medical applications.

Figure 2:
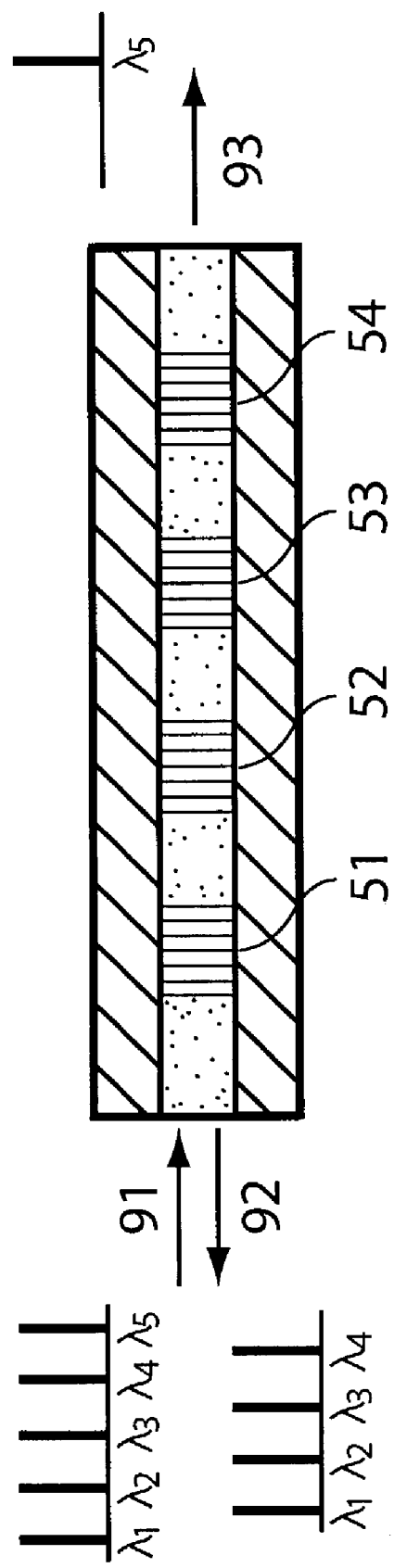
FIG. 2 is a cross section view of an optical fiber with multiple gratings, each grating with specific grating period reflecting a specific wavelength or bandwidth of the light.
Figure 3:
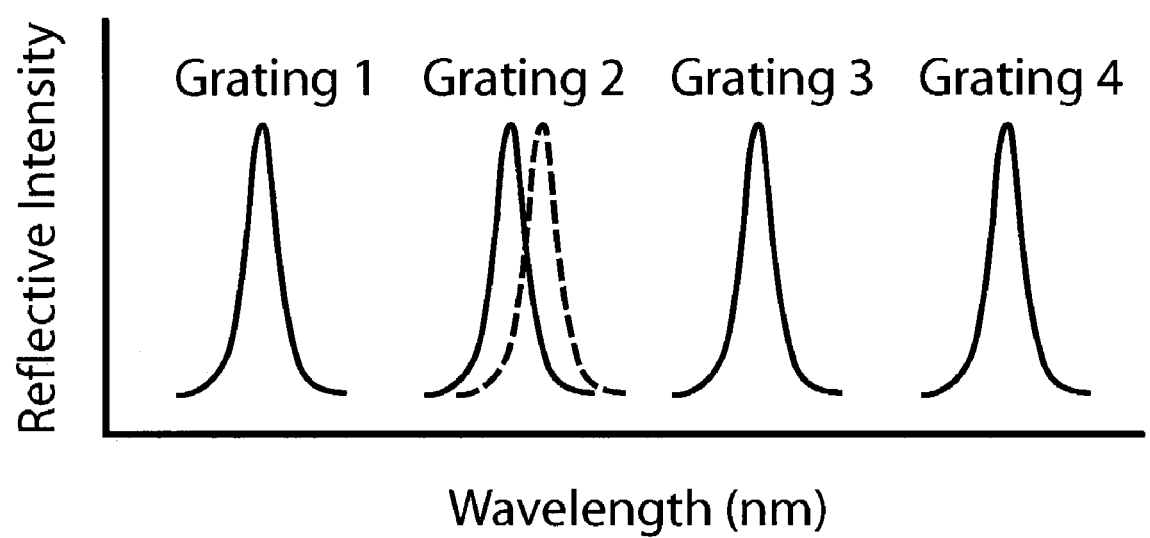
FIG. 3 shows multiple reflected wavelengths of the light from fiber gratings in a single optical fiber.
Figure 4:
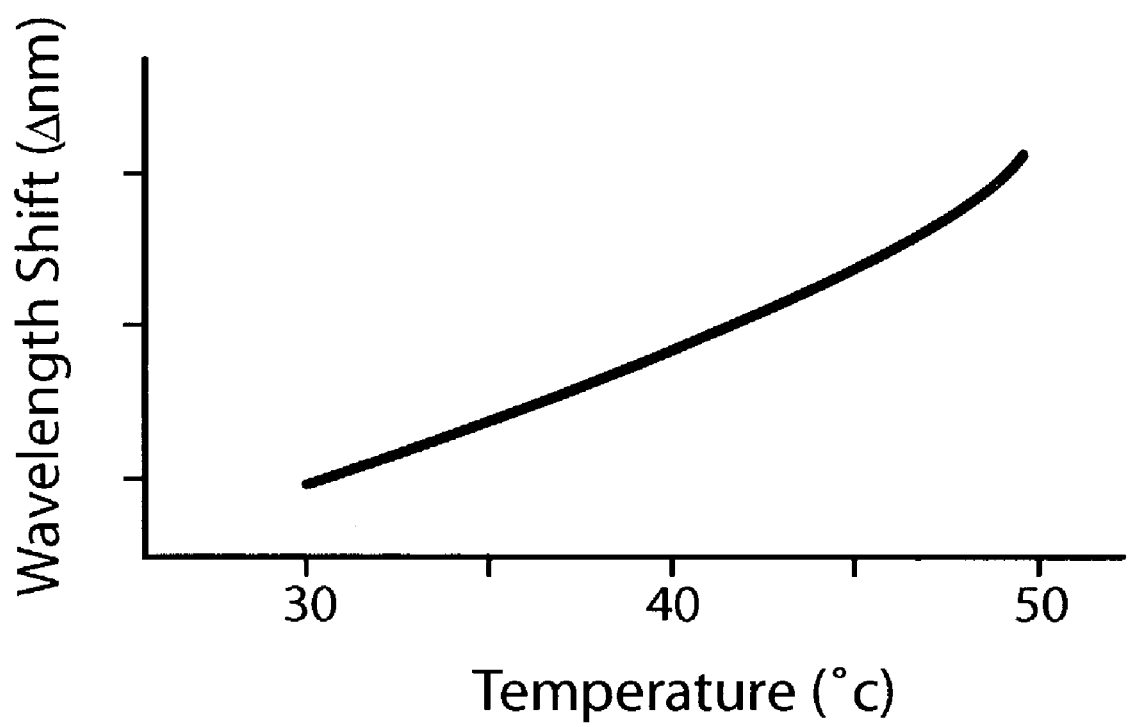
FIG. 4 is an illustrative graph shows a relationship between the wavelength shift and the temperature in the range of body temperature (30–50° C.).

Multiplexing of several grating 51, 52, 53, 54, as shown in FIG. 2, written in the same fiber 10 allows the creation of a distributed sensor capable of measuring the spatial profile of a temperature quantity. Each grating 51, 52, 53, 54, fabricated with different periodicity 32, reflects a specific wavelength. For illustration purposes, when a light beam 91 (with $\lambda_1$ to $\lambda_5$) from a broadband light source, an ultra wideband light source, or multiple-wavelength light source 98 (shown in FIG. 6) is input into the fiber, the multiple gratings reflect a first portion 92 ($\lambda_1$ to $\lambda_4$)) and transmit a second portion 93 ($\lambda_5$) of the light depending on the effective index of the grating. Therefore, by monitoring the shift of a specific reflected wavelength, for example, as shown in grating 2 of the FIG. 3, the local temperature in the vessel wall at that grating can be correlatively measured externally. The total length of each grating is about 1 to 5 mm, and the reflectivity can be greater than −20 db. FIG. 4 shows an example of the correlated wavelength shift versus temperature at 37° C. in the range of human body temperature. The actual correlative relationship between the wavelength shift and the temperature of a specific fiber device system could be calibrated and established when the fibers are in a simulated operating shape, configuration and conditions.

The temperature resolution of the intrinsic silica core fiber Bragg grating is approximately 0.01 nm/° C. To obtain a resolution of 0.1° C., the spectrum analyzer must resolve the shift of the reflected wavelength to an accuracy of about 0.001 nm. Various methods are commonly used to increase temperature resolution. The first method is to apply temperature sensitive materials or polymers, such as PMMA, onto the cladding 30 at grating area, thus leads to a large temperature change or a larger temperature coefficient (Δn/ΔT). The second method to enhance the temperature resolution is to use long-period grating. For typical Bragg grating, the grating periodicity (d) 32 is 0.5–10 μm, while for long period fiber grating (LPG), the periodicity can be as large as several hundred micrometers. The larger grating periodicity, d, in LPG will lead to a larger wavelength shift, Δλ. The higher order resonant peaks of LPG are very sensitive to its ambient refractive index. The wavelength shift of long period grating can be two to three orders of magnitude larger than that of Bragg grating. An LPG-based temperature sensor can easily achieve a resolution of about 0.01° C.

Figure 5:
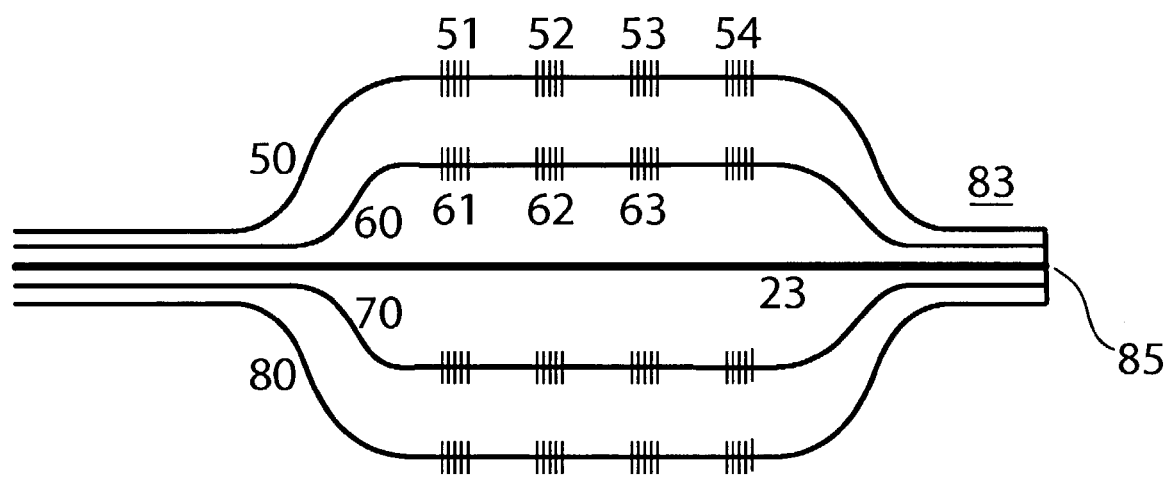
FIG. 5 shows the schematic diagram of a basket catheter with multiple optical fibers with multiple gratings for mapping the temperature distribution in a blood vessel.

FIG. 5 shows a distal portion basket arrangement of an optical thermal basket catheter loaded with multiple small and flexible optical fibers 50, 60, 70, 80, and each fiber is incorporated with multiple optical grating elements 51, 52, 53, 54, 61, 62, 63. A 3 or 4 French catheter or smaller with an expandable and externally controllable basket arrangement can support 4 to 10 fibers depending on the design dimension and configuration. One method to deploy and radially expand the optical fiber basket is to utilize a highly flexible pulling wire 23 (also shown in FIG. 8). The tip 85 of the pulling wire 23 is secured to the tip bundle 83 of the flexible optical fibers 50, 60, 70, 80.

To enhance the outward expansion property, the optical fibers may suitably be slightly preshaped. In some aspect of the present invention, the basket catheter may comprise an inflatable balloon sized and configured to expand the fibers radially outward during the deployment and temperature sensing state. In one further aspect of the present invention, each of the fibers may be supported intimately by an expandable wire during the deployment and temperature sensing state. The basket catheter 19 permits good thermal contact of the optical grating elements on the optical fiber with the arterial wall. Each optical fiber sensors (that is, optical grating elements) are sized, configured and suitably located on the optical fiber enabling optimal contact with the target inner surface of a blood vessel, allowing monitoring of temperature upon expansion and in contact with the vulnerable plaque. The total sensing length in each fiber is approximately 2–5 cm. The length of the optical fiber is comparable to the length of the catheter. By using an optical thermal basket catheter system, it does not need to drag the catheter for mapping a whole region of interest.

Figure 6:
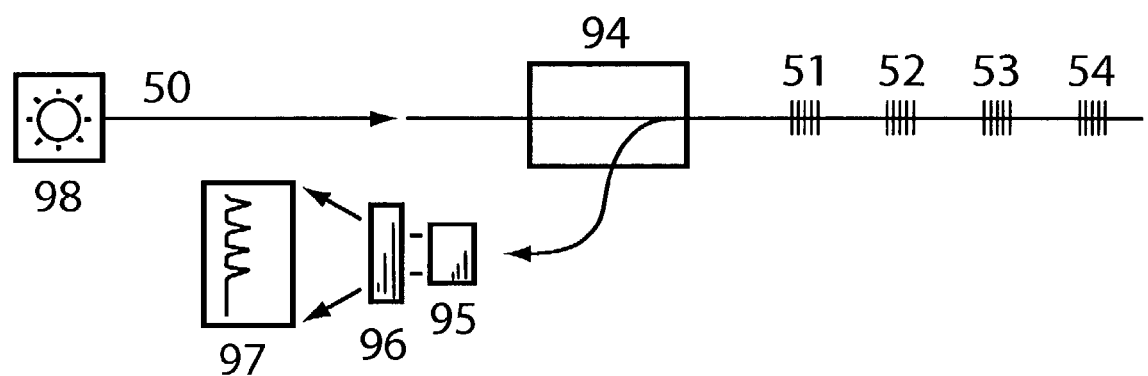
FIG. 6 shows the optoelectronic components of the optical thermal device system of the present invention for reflective wavelength measurement.

The optical thermal basket catheter system, as shown in FIG. 6, is integrated with a light source 98, a fiber splitting coupler 94, wavelength diffraction elements 96, and an optical signal detection system 97. Light from a broadband light-emitting diode (LED) or an ultra wideband light source travels through a single-mode fiber 50 to reach the grating 51, 52, 53, 54. Diode lasers, such as broadband diode lasers (1.3–1.55 μm) that cover the fiber communication wavelengths, are also available. Some lamp sources, such as a tungsten lamp, which are broadband light sources that cover the entire near infrared range, are also suitable as a continuous light source. Though the light source has a broad bandwidth; the reflected light from the grating is relatively narrow. The reflected light propagates back in the same fiber 50 and is coupled into a detection fiber by an optical coupler 94. Optical fiber couplers are used extensively in optical fiber communication systems. The most common couplers are fused fiber and directional coupler, which split the optical signal from one fiber into two fibers with different intensity ratio. The signal demultiplexing is constructed with a focusing/collimating lens 95, a diffraction grating 96, and a two dimensional CCD (charge coupled device) array 97.

The spectral peaks associated with each grating are physically separated by the diffraction grating 96 and illuminated on the CCD 97. The movement of the peak on CCD is related to the peak shift due to temperature change originated from fiber grating. When multiple signal fibers are aligned linearly in front of the entrance of the diffraction grating 96, a 2-D CCD provides the ability to simultaneously monitor multiple reflection spectra from multiple fibers. The detector 97 is interfaced through an analog-to-digital converter to an advanced signal processor in a computer. The real-time data acquisition software supports digital processing with a thermal resolution of 0.01° C. The temperature distributions obtained from the multiple sensors offer a thermographic mapping of the entire vessel walls. The circumferential and longitudinal thermal profiles of the vessel wall can also be displayed. The system is calibrated under simulated operating conditions to remove other non-thermal effects. In general, the data acquisition and analysis of the optical parameters are well known to an ordinary person who is skilled in the art.

Figure 7:
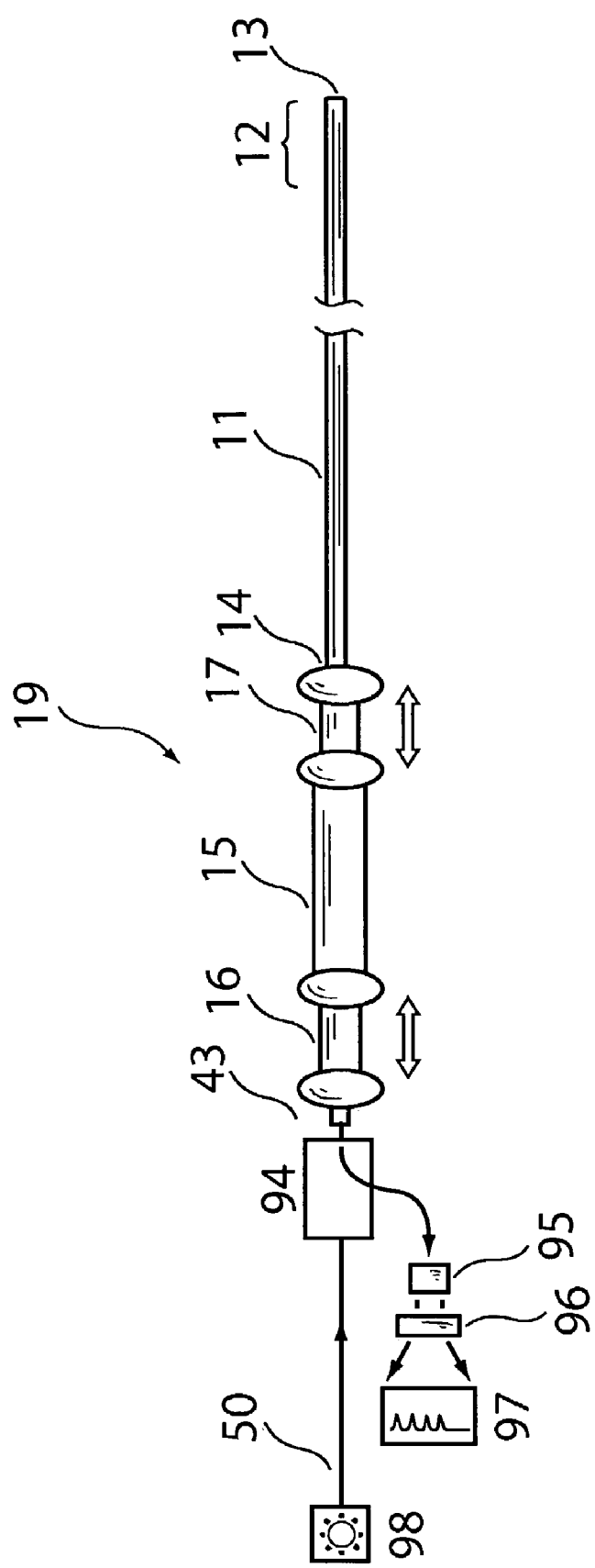
FIG. 7 is an overall view of the optical thermal device system having a deployable optical fiber assembly arrangement and the optoelectronic components, constructed in accordance with the principles of the present invention.

FIG. 7 shows an overall view of the optical thermal device system having a deployable optical fiber assembly arrangement and the optoelectronic components, constructed in accordance with the principles of the present invention. As shown in FIG. 7, one preferred embodiment of the thermal device system comprises an elongate tubular element (for example, a catheter shaft, a cannula, or a hollow needle) 11, the catheter shaft having a distal section 12, a shaft distal end 13, a shaft proximal end 14, and at least one lumen 18 extending between the shaft proximal end 14 and the shaft distal end 13, wherein the at least one lumen 18 may have at least one opening 71 at the shaft distal end 13 of the catheter shaft 11. A handle 15 is attached to the shaft proximal end 14 of the catheter shaft 11, wherein the handle 15 has a cavity for allowing at least one fiber 50, 60, 70, 80 and/or the pulling wire 23 to pass through.

In some aspect of the present invention, the optical thermal medical device 19 is for monitoring temperature of a tissue region of a patient without a need for dragging the device along the tissue wall. The device comprises an elongate tubular element comprising at least one optical fiber that contacts the tissue region; the at least one optical fiber having at least one optical grating along an axis of the fiber; and a light source having a light beam, wherein the light beam is coupled into the at least one optical fiber; wherein the at least one optical grating along the axis of the fiber reflects a certain wavelength or intensity of the light beam, the certain wavelength or intensity of the reflected light beam being correlated to the temperature of the tissue region.

Figure 8:
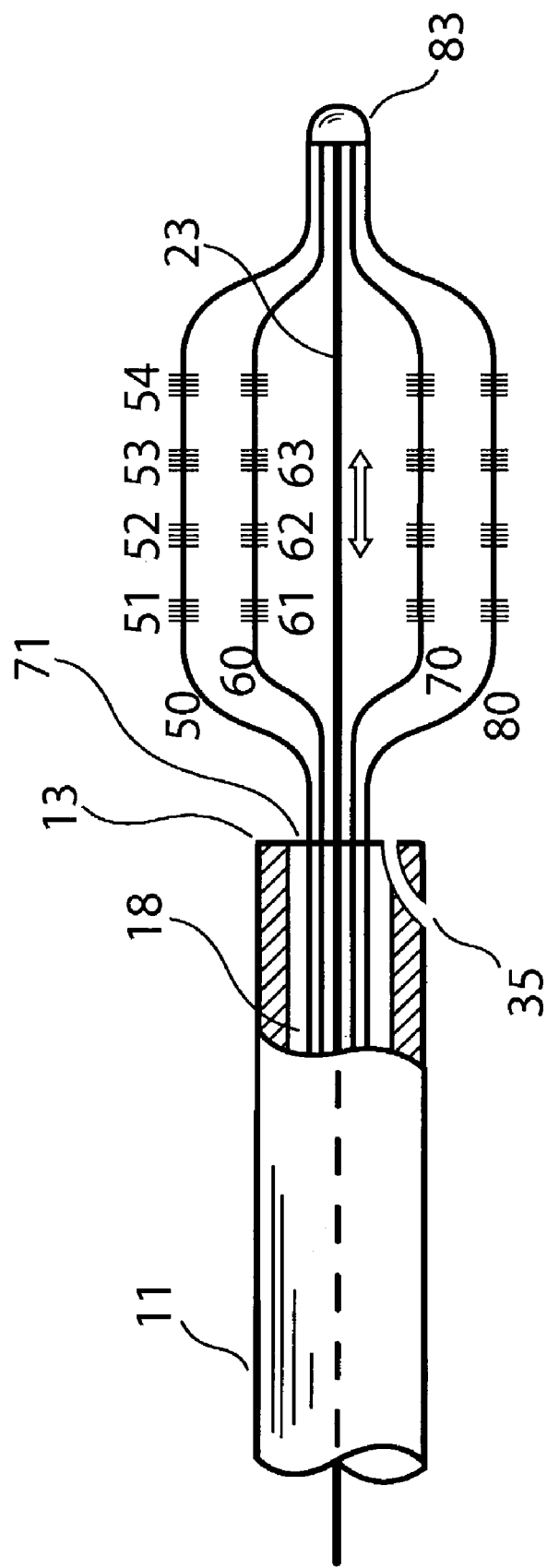
FIG. 8 is a cross-sectional view of the distal end portion of the device system of FIG. 7, the device system having a deployable optical fiber assembly arrangement positioned at the distal section of a flexible catheter shaft at a deployed state.

In one preferred embodiment, the optical thermal medical device is a basket catheter. As shown in FIG. 8, the optical thermal device system may comprise a pulling wire 23 inside the lumen 18 of the catheter shaft 11. The pulling wire or connecting wire 23 has a distal end and a proximal end, wherein the distal end of the pulling wire 23 is joined to the distal joint 83 of the basket fibers, and wherein the proximal end of the pulling wire is secured to the pulling mechanism 16 mounted on the handle 15. The pulling mechanism 16 may be a special push-pull controller or the like on the handle 15 adapted for the push-pull operation of the pulling wire 23. The fiber assembly arrangement, including an optical fiber bundles of fibers 50, 60, 70, 80 with gratings, is mounted at about the distal section 12 of the catheter shaft 11, wherein the fiber assembly arrangement comprises a plurality of preshaped expandable basket fiber members 50, 60, 70, 80, each basket fiber having a fiber distal end and a fiber proximal end, wherein the fiber distal ends of the preshaped expandable basket fibers are joined at a basket distal joint 83. The fiber assembly arrangement is associated the fiber assembly deployment mechanism 17, which is actuatable to deploy the arrangement out of the distal end opening 71 of the catheter shaft 11. Prior to activating the wire 23, the wire 23 is aligned in parallel with the fibers 50, 60, 70, 80. During deployment phase, the fibers are first deployed outside of the distal end 13 of the catheter by a deployment mechanism 17. When the wire 23 is pulled by a pulling mechanism 16 located at the handle 15 of the basket catheter 19 externally, the optical fibers will expand outwardly and form a basket.

The fiber assembly deployment mechanism 17 is mounted on the handle 15, wherein the fiber assembly deployment mechanism 17 is attached to the proximal end of the fiber bundle. The plurality of preshaped expandable basket fibers is suitably expanded at a deployed state, whereas the plurality of preshaped expandable basket fibers is retracted within the lumen 18 at a non-deployed state. During the insertion into or removal of the medical device from a patient, the fiber assembly arrangement is at a non-deployed state.

In some aspect, the device system further comprises a wire guide shaft at the distal section 12 of the catheter shaft 11, the wire guide shaft defining a wire guide lumen 35, the wire guide shaft having a proximal end and a distal end, wherein the wire guide lumen 35 has at least one opening at the distal end and at least one opening at the proximal end of the wire guide shaft, wherein the wire guide shaft is used for introducing the device system into a vascular vessel over a pre-introduced guidewire. The wire guide lumen 35 may be located close to one side of the wire guide shaft for rapid exchange of the optical fiber device system over the guidewire. For guiding the device system of the present invention into a blood vessel, the distal section 12 may further comprise an externally detectable imaging element, such as an ultrasound transducer, an electromagnetic chip, an MRI coil, a short range radiofrequency antenna, or the like.

Therefore in some aspect, it is provided an optical thermal basket catheter for monitoring temperature of a vessel wall of a patient comprising: (a) an elongate catheter sheath having a lumen, a distal sheath end, and a proximal sheath end; (b) a plurality of optical fibers deployably disposed within the lumen of the catheter sheath, each fiber having a distal fiber portion, a distal fiber end and a proximal fiber end, wherein the plurality of distal fiber portions is suitably expandable in an outwardly radial manner adapted for forming a basket shape and for contacting at least a portion of the vessel wall, each fiber having at least one optical grating along an axis of the fiber; and (c) a light source having a light beam, wherein the light beam is coupled into the plurality of optical fibers, wherein the at least one optical grating reflects a certain wavelength or intensity of the light beam, the certain wavelength or intensity of the reflected light beam being correlated to the temperature of the portion of the vessel wall.

In another preferred embodiment, the optical thermal device for monitoring temperature of a tissue region of a patient is a steerable or flexible probe. The probe comprises an elongate tubular element comprising at least one optical fiber that contacts the tissue region; the at least one optical fiber having at least one optical grating along an axis of the fiber; and a light source having a light beam, wherein the light beam is coupled into the at least one optical fiber; wherein the at least one optical grating along the axis of the fiber reflects a certain wavelength or intensity of the light beam, the certain wavelength or intensity of the reflected light beam being correlated to the temperature of the tissue region.

In some aspect, the elongate tubular element of the probe is a catheter, a cannula, or a hollow needle with side opening. The tissue region of interest comprises a vessel wall of a blood vessel, a heart or a breast of the patient. In another aspect, the optical grating is a long period grating or Bragg grating, wherein the optical grating is coated with a material having a thermal coefficient that is greater than a thermal coefficient of the fiber. The optical thermal device may further comprise an optical diffraction means for simultaneously measuring multiple peaks of the reflected light beam. Typically, the optical grating has a length between 0.2 and 40 mm, whereas the probe has a temperature resolution between 0.01 to 1.0° C.

Figure 9A:
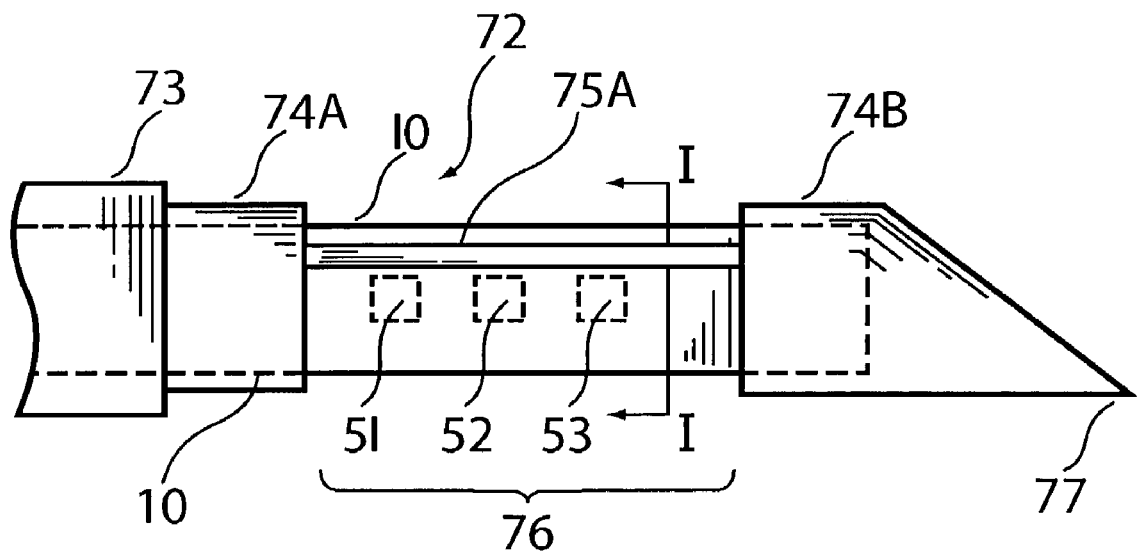
FIG. 9A is one embodiment of a hollow needle probe with side opening.

FIG. 9A shows one embodiment of a hollow needle probe 72 with side opening 76, wherein the surface of an enclosed optic fiber 10 is exposed to and contacts with the surrounding tissue through the opening 76. In a preferred embodiment, the needle probe 72 comprises a handle 73 and a needle body that is hollow, wherein the needle body is comprised of a distal needle portion 74B, a proximal needle portion 74A and at least two connecting bars 75A, 75B securely coupling the distal needle portion 74B and the proximal needle portion 74A. Further, the proximal needle portion 74A is securely attached to the handle 73. The distal needle portion 74B further comprises a penetrating end 77 that is suitably sharpened for easily penetrating into and through tissue, such as a heart or a breast.

Figure 9B:
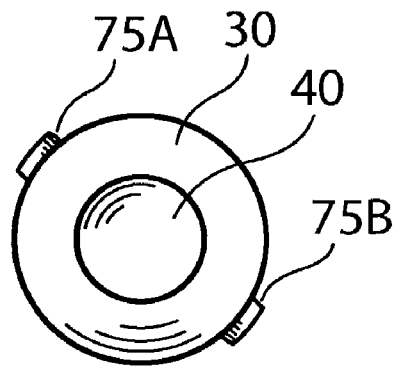
FIG. 9B is a side cross-sectional view of the needle probe, section I—I of FIG. 9A.

Within the hollow cavity of the needle body, there provides an optic fiber 10 with gratings 51, 52, 53. FIG. 9B shows a side cross-sectional view of the needle probe 72, section I—I of FIG. 9A. The optic fiber 10 comprises the cladding 30 and the core 40. In one aspect, the optic fiber is securely held within the needle body in a way such that the surface of the fiber is exposed to a target tissue for mapping the tissue temperature or detecting the diseases, for example, the breast tumor or cancer. In another aspect, the optic fiber 10 is integrated with a light source, a fiber splitting coupler, wavelength diffraction elements, and an optical signal detection system as described above in FIG. 6.

The optical fiber sensors system has several operational advantages including immunity to electromagnetic interference, high flexibility, remote sensing capability, smaller size of sensing element, lightweight, and easy to fabricate. It is one preferred aspect of the present invention to provide an optical fiber sensor for chemical composition, stress-strain tissue elasticity, temperature and pressure sensing of the blood vessel wall related to vulnerable plaque.

From the foregoing, it should now be appreciated that an optical thermal mapping device comprising at least one optical fiber with at least one optical grating for simultaneously monitoring the thermal distribution of and detecting vulnerable plaque within a blood vessel has been disclosed. It is also generally applicable for monitoring temperature in a body vessel or channel, in a breast, in a heart, or in other tissue. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

The invention claimed is:

1. An optical thermal basket catheter system for monitoring temperature of a vessel wall of a patient comprising:
   a. an elongate catheter sheath having a lumen, a distal sheath end, and a proximal sheath end;
   b. a plurality of optical fibers deployably disposed within the lumen of said catheter sheath, each fiber having a distal fiber portion, a distal fiber end and a proximal fiber end, wherein said plurality of distal fiber portions is suitably expandable in an outwardly radial manner forming a basket shape and contacting at least a portion of the vessel wall, each fiber having at least one optical grating along an axis of the fiber; and
   c. a light source having a light beam, wherein the light beam is coupled into said plurality of optical fibers, wherein said at least one optical grating reflects a certain wavelength or intensity of said light beam, said certain wavelength or intensity of the reflected light beam being correlated to the temperature of said portion of the vessel wall.

2. The optical thermal basket catheter system of claim 1, wherein said optical grating is a Bragg grating or a long period grating.

3. The optical thermal basket catheter system of claim 1, wherein said optical grating is coated with a material having a thermal coefficient that is greater than a thermal coefficient of the fiber.

4. The optical thermal basket catheter system of claim 1 further comprising an optical diffraction means for simultaneously measuring multiple peaks of said reflected light beam.

5. The optical thermal basket catheter system of claim 1, wherein said optical grating has a length between 0.2 and 40 mm.

6. The optical thermal basket catheter system of claim 1, wherein said plurality of optical fibers has a temperature resolution between 0.01 to 1.0° C.

7. A method for monitoring temperature of a tissue region of a patient, the method comprising: deploying an elongate tubular element into contacting said tissue region, wherein said elongate tubular element comprises at least one optical fiber; said fiber having at least one optical grating along an axis of said fiber, and wherein a light source having a light beam is coupled into said at least one optical fiber; said optical grating reflecting a certain wavelength or intensity of said light beam, and said certain wavelength or intensity of the reflected light beam being correlated to the temperature of the tissue region; and monitoring a temperature differential between a first temperature correlated from a first of said at least one optical grating and a second temperature correlated from a second of said at least one optical grating.

8. The method of claim 7, wherein the tissue region is a vessel wall of a blood vessel.

9. The method of claim 7, wherein the tissue region is vulnerable plaque of a blood vessel.

10. The method of claim 7, wherein said elongate tubular element is a catheter or a cannula.

11. The method of claim 7, wherein said elongate tubular element is a hollow needle with a-side opening.

12. The method of claim 7, wherein said tissue region is a heart of the patient.

13. The method of claim 7, wherein said tissue region is a breast of the patient.

14. The method of claim 7, wherein said optical grains is a Bragg grating.

15. The method of claim 7, wherein said optical grating is a long period grating.

16. The method of claim 7, wherein said optical grating is coated with a material having a thermal coefficient that is greater than a thermal coefficient of the fiber.

17. The method of claim 7, further comprising an optical diffraction means for simultaneously measuring multiple peaks of said reflected light beam.

18. The method of claim 7, wherein said optical grating has a length between 0.2 and 40 mm.

19. The method of claim 7, wherein said device has a temperature resolution between 0.01 to 1.0° C.

* * * * *